(12) United States Patent
Harrison et al.

(10) Patent No.: US 10,849,771 B2
(45) Date of Patent: Dec. 1, 2020

(54) STENT DELIVERY SYSTEMS AND METHODS FOR MAKING AND USING STENT DELIVERY SYSTEMS

(75) Inventors: Jim G. Harrison, Cloverdale, IN (US); Steve A. Pickett, Spencer, IN (US); Leslie P. Sherwood, Ellettsville, IN (US); Marsha M. Weiner, Terre Haute, IN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1021 days.

(21) Appl. No.: 13/534,788

(22) Filed: Jun. 27, 2012

(65) Prior Publication Data
US 2012/0330397 A1  Dec. 27, 2012

Related U.S. Application Data

(60) Provisional application No. 61/501,387, filed on Jun. 27, 2011.

(51) Int. Cl.
*A61F 2/95* (2013.01)
*A61F 2/04* (2013.01)

(52) U.S. Cl.
CPC .......... *A61F 2/95* (2013.01); *A61F 2002/041* (2013.01); *A61F 2002/9505* (2013.01)

(58) Field of Classification Search
CPC ............... A61F 2/95; A61F 2002/9505; A61F 2/962–966; A61F 2002/9511; A61F 2002/9665
USPC ...................................................... 623/1.11
See application file for complete search history.

(56) References Cited

U.S. PATENT DOCUMENTS

| | | |
|---|---|---|
| 1,204,053 A | 11/1916 | Moore |
| 2,212,334 A | 8/1940 | Wallerich |
| 2,393,003 A | 1/1946 | Smith |
| 2,623,520 A | 12/1952 | Bamford, Jr. et al. |
| 3,015,869 A | 1/1962 | Rapata |
| 3,100,490 A | 8/1963 | Desautels |
| 3,332,424 A | 7/1967 | Minteer |
| 3,421,509 A | 1/1969 | Fiore |
| 3,460,541 A | 8/1969 | Doherty |
| 3,536,281 A | 10/1970 | Meehan et al. |
| 3,592,197 A | 7/1971 | Cohen |

(Continued)

FOREIGN PATENT DOCUMENTS

| | | |
|---|---|---|
| AU | 620320 | 2/1992 |
| CA | 1112119 | 11/1981 |

(Continued)

OTHER PUBLICATIONS

US 5,171,298 A, 12/1992, Walker et al. (withdrawn)

(Continued)

*Primary Examiner* — Shaun L David (57) ABSTRACT

Stent delivery systems and methods for making and using stent delivery systems are disclosed. An example stent delivery system may include a guide catheter. A push catheter may be slidably disposed over the guide catheter. A stent may be slidably disposed over the guide catheter and disposed adjacent to a distal end of the push catheter. An attachment mechanism may be coupled to the push catheter that is configured to engage the stent. The attachment mechanism may include a base and at least one cantilever extending from the base.

19 Claims, 7 Drawing Sheets

(56) References Cited

U.S. PATENT DOCUMENTS

| | | |
|---|---|---|
| 3,707,151 A | 12/1972 | Jackson |
| 3,783,453 A | 1/1974 | Bolie |
| 3,889,686 A | 6/1975 | Duturbure |
| 3,890,977 A | 6/1975 | Wilson |
| 3,908,635 A | 9/1975 | Viek |
| 3,938,529 A | 2/1976 | Gibbons |
| 3,970,089 A | 7/1976 | Saice |
| 3,995,642 A | 12/1976 | Adair |
| 4,194,513 A | 3/1980 | Rhine et al. |
| 4,212,304 A | 7/1980 | Finney |
| 4,225,979 A | 10/1980 | Rey et al. |
| 4,242,304 A | 12/1980 | Ryder |
| 4,248,214 A | 2/1981 | Hannah et al. |
| 4,299,226 A | 11/1981 | Banka |
| 4,307,723 A | 12/1981 | Finney |
| 4,334,327 A | 6/1982 | Lyman et al. |
| 4,345,606 A | 8/1982 | Littleford |
| 4,364,392 A | 12/1982 | Strother et al. |
| 4,382,445 A | 5/1983 | Sommers |
| 4,411,654 A | 10/1983 | Boarini et al. |
| 4,412,832 A | 11/1983 | Kling et al. |
| 4,413,989 A | 11/1983 | Schjeldahl et al. |
| 4,423,725 A | 1/1984 | Baran et al. |
| 4,425,919 A | 1/1984 | Alston, Jr. et al. |
| 4,434,797 A | 3/1984 | Silander |
| 4,445,892 A | 5/1984 | Hussein et al. |
| 4,474,569 A | 10/1984 | Newkirk |
| 4,484,585 A | 11/1984 | Baier |
| 4,500,313 A | 2/1985 | Young |
| RE31,855 E | 3/1985 | Osborne |
| 4,531,933 A | 7/1985 | Norton et al. |
| 4,545,373 A | 10/1985 | Christoudias |
| 4,554,929 A | 11/1985 | Samson et al. |
| 4,568,338 A | 2/1986 | Todd |
| 4,573,470 A | 3/1986 | Samson et al. |
| 4,581,017 A | 4/1986 | Sahota |
| 4,582,181 A | 4/1986 | Samson |
| 4,592,341 A | 6/1986 | Omagari et al. |
| 4,606,347 A | 8/1986 | Fogarty et al. |
| 4,610,657 A | 9/1986 | Densow |
| 4,616,653 A | 10/1986 | Samson et al. |
| 4,641,654 A | 2/1987 | Samson et al. |
| 4,643,716 A | 2/1987 | Drach |
| 4,645,493 A | 2/1987 | Ferrando et al. |
| 4,646,742 A | 3/1987 | Packard et al. |
| 4,654,025 A | 3/1987 | Cassou et al. |
| 4,655,746 A | 4/1987 | Daniels et al. |
| 4,655,771 A | 4/1987 | Wallsten |
| 4,671,795 A | 6/1987 | Mulchin |
| 4,684,369 A | 8/1987 | Wildemeersch |
| 4,696,668 A | 9/1987 | Wilcox |
| 4,699,611 A | 10/1987 | Bowden |
| 4,713,049 A | 12/1987 | Carter |
| 4,723,550 A | 2/1988 | Bales et al. |
| 4,738,667 A | 4/1988 | Galloway |
| 4,747,833 A | 5/1988 | Kousai et al. |
| 4,748,982 A | 6/1988 | Horzewski et al. |
| 4,755,175 A | 7/1988 | Nilsson |
| 4,762,128 A | 8/1988 | Rosenbluth |
| 4,762,129 A | 8/1988 | Bonzel |
| 4,763,654 A | 8/1988 | Jang |
| 4,771,777 A | 9/1988 | Horzewski et al. |
| 4,781,677 A | 11/1988 | Wilcox |
| 4,783,454 A | 11/1988 | Liu |
| 4,784,651 A | 11/1988 | Hickey |
| 4,787,884 A | 11/1988 | Goldberg |
| 4,790,315 A | 12/1988 | Mueller, Jr. et al. |
| 4,790,809 A | 12/1988 | Kuntz |
| 4,790,810 A | 12/1988 | Pugh, Jr. et al. |
| 4,798,193 A | 1/1989 | Giesy et al. |
| 4,798,594 A | 1/1989 | Hillstead |
| 4,813,925 A | 3/1989 | Anderson, Jr. et al. |
| 4,813,934 A | 3/1989 | Engelson et al. |
| 4,817,613 A | 4/1989 | Jaraczewski et al. |
| 4,819,751 A | 4/1989 | Shimada et al. |
| 4,820,262 A | 4/1989 | Finney |
| 4,822,333 A | 4/1989 | Lavarenne |
| 4,824,435 A | 4/1989 | Giesy et al. |
| 4,832,055 A | 5/1989 | Palestrant |
| 4,835,824 A | 6/1989 | Durham et al. |
| 4,838,268 A | 6/1989 | Keith et al. |
| 4,844,092 A | 7/1989 | Rydell et al. |
| 4,846,174 A | 7/1989 | Willard et al. |
| 4,846,193 A | 7/1989 | Tremulis et al. |
| 4,848,343 A | 7/1989 | Wallsten et al. |
| 4,848,344 A | 7/1989 | Sos et al. |
| 4,874,360 A | 10/1989 | Goldberg et al. |
| 4,877,031 A | 10/1989 | Conway et al. |
| 4,886,065 A | 12/1989 | Collins, Jr. |
| 4,892,519 A | 1/1990 | Songer et al. |
| 4,898,577 A | 2/1990 | Badger et al. |
| 4,900,184 A | 2/1990 | Cleveland |
| 4,905,667 A | 3/1990 | Foerster et al. |
| 4,906,241 A | 3/1990 | Noddin et al. |
| 4,913,141 A | 4/1990 | Hillstead |
| 4,913,683 A | 4/1990 | Gregory |
| 4,917,088 A | 4/1990 | Crittenden |
| 4,917,103 A | 4/1990 | Gambale et al. |
| 4,917,666 A | 4/1990 | Solar et al. |
| 4,927,418 A | 5/1990 | Dake et al. |
| 4,928,693 A | 5/1990 | Goodin et al. |
| 4,931,037 A | 6/1990 | Wetterman |
| 4,932,413 A | 6/1990 | Shockey et al. |
| 4,932,959 A | 6/1990 | Horzewski et al. |
| 4,944,745 A | 7/1990 | Sogard et al. |
| 4,946,443 A | 8/1990 | Hauser et al. |
| 4,950,228 A | 8/1990 | Knapp, Jr. et al. |
| 4,955,858 A | 9/1990 | Drews |
| 4,955,895 A | 9/1990 | Sugiyama et al. |
| 4,957,479 A | 9/1990 | Roemer |
| 4,963,129 A | 10/1990 | Rusch |
| 4,964,409 A | 10/1990 | Tremulis |
| 4,967,753 A | 11/1990 | Haase et al. |
| 4,973,301 A | 11/1990 | Nissenkorn |
| 4,976,720 A | 12/1990 | Machold et al. |
| 4,983,168 A | 1/1991 | Moorehead |
| 4,986,814 A | 1/1991 | Burney et al. |
| 4,988,356 A | 1/1991 | Crittenden et al. |
| 4,990,133 A | 2/1991 | Solazzo |
| 4,990,151 A | 2/1991 | Wallsten |
| 4,994,027 A | 2/1991 | Farrell |
| 4,994,066 A | 2/1991 | Voss |
| 4,997,421 A | 3/1991 | Palsrok et al. |
| 4,998,917 A | 3/1991 | Gaiser et al. |
| 4,998,923 A | 3/1991 | Samson et al. |
| 5,002,532 A | 3/1991 | Gaiser et al. |
| 5,003,990 A | 4/1991 | Osypka |
| 5,007,901 A | 4/1991 | Shields |
| 5,015,231 A | 5/1991 | Keith et al. |
| 5,019,085 A | 5/1991 | Hillstead |
| 5,019,102 A | 5/1991 | Hoene |
| 5,026,377 A | 6/1991 | Burton et al. |
| 5,026,607 A | 6/1991 | Kiezulas |
| 5,031,636 A | 7/1991 | Gambale et al. |
| 5,032,113 A | 7/1991 | Burns |
| 5,035,705 A | 7/1991 | Burns |
| 5,040,548 A | 8/1991 | Yock |
| 5,042,985 A | 8/1991 | Elliott et al. |
| 5,045,061 A | 9/1991 | Seifert et al. |
| 5,046,497 A | 9/1991 | Millar |
| 5,047,018 A | 9/1991 | Gay et al. |
| 5,047,045 A | 9/1991 | Arney et al. |
| 5,052,998 A | 10/1991 | Zimmon |
| 5,057,092 A | 10/1991 | Webster, Jr. |
| 5,061,267 A | 10/1991 | Zeiher |
| 5,061,273 A | 10/1991 | Yock |
| 5,064,414 A | 11/1991 | Revane |
| 5,066,285 A | 11/1991 | Hillstead |
| 5,078,681 A | 1/1992 | Kawashima |
| 5,085,636 A | 2/1992 | Burns |
| 5,090,958 A | 2/1992 | Sahota |
| 5,098,374 A | 3/1992 | Othel-Jacobsen et al. |
| 5,114,403 A | 5/1992 | Clarke et al. |
| 5,116,309 A | 5/1992 | Coll |

(56) References Cited

U.S. PATENT DOCUMENTS

| | | |
|---|---|---|
| 5,120,308 A | 6/1992 | Hess |
| 5,125,905 A | 6/1992 | Wright et al. |
| 5,125,915 A | 6/1992 | Berry et al. |
| 5,135,494 A | 8/1992 | Engelson et al. |
| 5,135,535 A | 8/1992 | Kramer |
| 5,141,502 A | 8/1992 | Macaluso, Jr. |
| 5,141,518 A | 8/1992 | Hess et al. |
| 5,147,370 A | 9/1992 | McNamara et al. |
| 5,147,377 A | 9/1992 | Sahota |
| 5,152,749 A | 10/1992 | Giesy et al. |
| 5,154,725 A | 10/1992 | Leopold |
| 5,158,545 A | 10/1992 | Trudell et al. |
| 5,160,321 A | 11/1992 | Sahota |
| 5,160,341 A | 11/1992 | Brenneman et al. |
| 5,167,634 A | 12/1992 | Corrigan, Jr. et al. |
| 5,171,221 A | 12/1992 | Samson |
| 5,171,222 A | 12/1992 | Euteneuer et al. |
| 5,176,637 A | 1/1993 | Sagae |
| 5,180,367 A | 1/1993 | Kontos et al. |
| 5,181,921 A | 1/1993 | Makita et al. |
| 5,195,978 A | 3/1993 | Schiffer |
| 5,205,822 A | 4/1993 | Johnson et al. |
| 5,209,728 A | 5/1993 | Kraus et al. |
| 5,217,434 A | 6/1993 | Arney |
| 5,217,482 A | 6/1993 | Keith |
| 5,221,260 A | 6/1993 | Burns et al. |
| 5,232,445 A | 8/1993 | Bonzel |
| 5,234,437 A | 8/1993 | Sepetka |
| 5,242,396 A | 9/1993 | Evard |
| 5,248,306 A | 9/1993 | Clark et al. |
| 5,250,033 A | 10/1993 | Evans et al. |
| 5,250,071 A | 10/1993 | Palermo |
| 5,256,144 A | 10/1993 | Kraus et al. |
| 5,261,916 A | 11/1993 | Engelson |
| 5,267,958 A | 12/1993 | Buchbinder et al. |
| 5,277,199 A | 1/1994 | DuBois et al. |
| 5,279,562 A | 1/1994 | Sirhan et al. |
| 5,282,479 A | 2/1994 | Havran |
| 5,282,784 A | 2/1994 | Willard |
| 5,290,232 A | 3/1994 | Johnson et al. |
| 5,290,241 A | 3/1994 | Kraus et al. |
| 5,290,247 A | 3/1994 | Crittenden |
| 5,295,954 A | 3/1994 | Sachse |
| 5,300,085 A | 4/1994 | Yock |
| 5,304,195 A | 4/1994 | Twyford, Jr. et al. |
| 5,304,198 A | 4/1994 | Samson |
| 5,306,247 A | 4/1994 | Pfenninger |
| 5,308,318 A | 5/1994 | Plassche, Jr. |
| 5,320,602 A | 6/1994 | Karpiel |
| 5,320,604 A | 6/1994 | Walker et al. |
| 5,322,501 A | 6/1994 | Mahmud-Durrani |
| 5,324,259 A | 6/1994 | Taylor et al. |
| 5,324,269 A | 6/1994 | Miraki |
| 5,328,468 A | 7/1994 | Kaneko et al. |
| 5,334,143 A | 8/1994 | Carroll |
| 5,334,185 A | 8/1994 | Giesy et al. |
| 5,334,187 A | 8/1994 | Fischell et al. |
| 5,346,467 A | 9/1994 | Coll |
| 5,348,537 A | 9/1994 | Wiesner et al. |
| 5,350,395 A | 9/1994 | Yock |
| 5,354,263 A | 10/1994 | Coll |
| 5,360,401 A | 11/1994 | Turnland |
| 5,364,340 A | 11/1994 | Coll |
| 5,364,354 A | 11/1994 | Walker et al. |
| 5,364,355 A | 11/1994 | Alden et al. |
| 5,364,376 A | 11/1994 | Horzewski et al. |
| 5,370,623 A | 12/1994 | Kreamer |
| 5,370,655 A | 12/1994 | Burns |
| 5,372,600 A | 12/1994 | Beyar et al. |
| 5,382,234 A | 1/1995 | Cornelius et al. |
| 5,454,790 A | 1/1995 | Dubrul |
| 5,389,087 A | 2/1995 | Miraki |
| 5,391,155 A | 2/1995 | Sachse |
| 5,395,335 A | 3/1995 | Jang |
| 5,397,302 A | 3/1995 | Weaver et al. |
| 5,401,257 A | 3/1995 | Chevalier, Jr. et al. |
| 5,405,378 A | 4/1995 | Strecker |
| 5,407,435 A | 4/1995 | Sachse |
| 5,409,468 A | 4/1995 | Sachse |
| 5,425,711 A | 6/1995 | Ressemann et al. |
| 5,451,233 A | 9/1995 | Yock |
| 5,454,788 A | 10/1995 | Walker et al. |
| 5,456,680 A | 10/1995 | Taylor et al. |
| 5,458,584 A | 10/1995 | Ginn et al. |
| 5,458,605 A | 10/1995 | Klemm |
| 5,458,613 A | 10/1995 | Gharibadeh et al. |
| 5,458,615 A | 10/1995 | Klemm et al. |
| 5,470,315 A | 11/1995 | Adams |
| 5,476,505 A | 12/1995 | Limon |
| 5,480,389 A | 1/1996 | McWha et al. |
| 5,480,434 A | 1/1996 | Eckstein et al. |
| 5,484,409 A | 1/1996 | Atkinson et al. |
| 5,484,444 A | 1/1996 | Braunschweiler et al. |
| 5,489,271 A | 2/1996 | Andersen |
| 5,490,837 A | 2/1996 | Blaeser et al. |
| 5,496,275 A | 3/1996 | Sirhan et al. |
| 5,496,344 A | 3/1996 | Kanesaka et al. |
| 5,496,346 A | 3/1996 | Horzewski et al. |
| 5,501,227 A | 3/1996 | Yock |
| 5,507,768 A | 4/1996 | Lau et al. |
| 5,531,700 A | 7/1996 | Moore et al. |
| 5,533,968 A | 7/1996 | Muni et al. |
| 5,536,248 A | 7/1996 | Weaver et al. |
| 5,540,236 A | 7/1996 | Ginn |
| 5,545,134 A | 8/1996 | Hilaire et al. |
| 5,545,138 A | 8/1996 | Fugoso et al. |
| 5,549,552 A | 8/1996 | Peters et al. |
| 5,569,201 A | 10/1996 | Burns |
| 5,578,009 A | 11/1996 | Kraus et al. |
| 5,599,291 A | 2/1997 | Balbierz et al. |
| 5,599,299 A | 2/1997 | Weaver et al. |
| 5,599,300 A | 2/1997 | Weaver et al. |
| 5,626,600 A | 5/1997 | Horzewski et al. |
| 5,639,274 A | 6/1997 | Fischell et al. |
| 5,643,278 A | 7/1997 | Wijay |
| 5,645,533 A | 7/1997 | Blaeser et al. |
| 5,653,748 A | 8/1997 | Strecker |
| 5,669,880 A | 9/1997 | Solar |
| 5,676,654 A | 10/1997 | Ellis et al. |
| 5,681,274 A | 10/1997 | Perkins et al. |
| 5,690,642 A | 11/1997 | Osborne et al. |
| 5,690,644 A | 11/1997 | Yurek et al. |
| 5,693,015 A | 12/1997 | Walker et al. |
| 5,695,468 A | 12/1997 | Lafontaine et al. |
| 5,702,439 A | 12/1997 | Keith et al. |
| 5,706,827 A | 1/1998 | Ehr et al. |
| 5,709,703 A | 1/1998 | Lukic et al. |
| 5,725,504 A | 3/1998 | Collins |
| 5,743,874 A | 4/1998 | Fischell et al. |
| 5,772,609 A | 6/1998 | Nguyen et al. |
| 5,776,099 A | 7/1998 | Tremulis |
| 5,782,855 A | 7/1998 | Lau et al. |
| 5,788,681 A | 8/1998 | Weaver et al. |
| 5,800,414 A | 9/1998 | Cazal |
| 5,833,706 A | 11/1998 | St. Germain et al. |
| 5,843,028 A | 12/1998 | Weaver et al. |
| 5,849,016 A | 12/1998 | Suhr |
| 5,921,952 A | 7/1999 | Desmond, III et al. |
| 5,921,971 A | 7/1999 | Agro et al. |
| 5,947,927 A | 9/1999 | Mertens |
| 5,980,533 A | 11/1999 | Holman |
| 6,007,522 A | 12/1999 | Agro et al. |
| 6,059,752 A | 5/2000 | Segal |
| 6,077,295 A | 6/2000 | Limon et al. |
| 6,095,990 A | 8/2000 | Parodi |
| 6,096,009 A | 8/2000 | Windheuser et al. |
| 6,113,607 A | 9/2000 | Lau et al. |
| 6,139,510 A | 10/2000 | Palermo |
| 6,152,910 A | 11/2000 | Agro et al. |
| 6,159,195 A | 12/2000 | Ha et al. |
| 6,248,100 B1 | 6/2001 | de Toledo et al. |
| 6,264,624 B1 | 7/2001 | Desmond, III et al. |
| 6,309,379 B1 | 10/2001 | Willard et al. |
| 6,346,093 B1 | 2/2002 | Allman et al. |

(56) References Cited

U.S. PATENT DOCUMENTS

| | | |
|---|---|---|
| 6,380,457 B1 | 4/2002 | Yurek et al. |
| 6,394,141 B2 | 5/2002 | Wages et al. |
| 6,398,799 B2 | 6/2002 | Kramer |
| 6,475,187 B1 | 11/2002 | Gerberding |
| 6,488,694 B1 | 12/2002 | Lau et al. |
| 6,527,789 B1 | 3/2003 | Lau et al. |
| 6,562,024 B2 | 5/2003 | Alvarez de Toledo et al. |
| 6,582,401 B1 | 6/2003 | Windheuser et al. |
| 6,582,459 B1 | 6/2003 | Lau et al. |
| 6,592,549 B2 | 7/2003 | Gerdts et al. |
| 6,723,071 B2 | 4/2004 | Gerdts et al. |
| 6,743,217 B2 | 6/2004 | Rowland et al. |
| 6,764,484 B2 | 7/2004 | Richardson et al. |
| 6,858,034 B1* | 2/2005 | Hijlkema et al. ............ 606/108 |
| 6,890,317 B2 | 5/2005 | Gerdts et al. |
| 7,001,358 B2 | 2/2006 | Fitzmaurice et al. |
| 7,115,109 B2 | 10/2006 | Gerdts et al. |
| 7,468,053 B2 | 12/2008 | Gerdts et al. |
| 7,550,002 B2 | 6/2009 | Goto et al. |
| 7,815,601 B2 | 10/2010 | Jordan et al. |
| 2002/0029076 A1* | 3/2002 | Yee .............................. 623/1.11 |
| 2004/0093061 A1* | 5/2004 | Acosta et al. ............... 623/1.11 |
| 2005/0085891 A1 | 4/2005 | Goto et al. |
| 2005/0085892 A1* | 4/2005 | Goto et al. .................. 623/1.12 |
| 2006/0276873 A1 | 12/2006 | Sato |
| 2007/0282436 A1* | 12/2007 | Pinchuk ................ A61F 2/2418 |
| | | 623/2.11 |
| 2007/0293929 A1* | 12/2007 | Aoba ........................ A61F 2/95 |
| | | 623/1.11 |
| 2008/0167628 A1 | 7/2008 | Li et al. |
| 2008/0300667 A1* | 12/2008 | Hebert et al. ................ 623/1.11 |
| 2009/0105808 A1 | 4/2009 | Gerdts et al. |
| 2009/0254165 A1* | 10/2009 | Tabor et al. .................. 623/1.11 |
| 2009/0312829 A1* | 12/2009 | Aoba et al. .................. 623/1.11 |
| 2011/0264203 A1* | 10/2011 | Dwork et al. ................ 623/2.11 |
| 2011/0301702 A1* | 12/2011 | Rust ...................... A61F 2/2418 |
| | | 623/2.11 |
| 2011/0313404 A1 | 12/2011 | Amos et al. |
| 2012/0095544 A1* | 4/2012 | Jeffrey ......................... 623/1.12 |
| 2012/0203325 A1 | 8/2012 | Weisman et al. |
| 2013/0274870 A1* | 10/2013 | Lombardi ............ A61F 2/2418 |
| | | 623/2.11 |

FOREIGN PATENT DOCUMENTS

| | | |
|---|---|---|
| DE | 3345612 | 6/1985 |
| DE | 3919740 | 12/1990 |
| DE | 41 15 007 | 11/1992 |
| EP | 0 328 760 | 8/1989 |
| EP | 0 388 112 | 9/1990 |
| EP | 0 405 831 | 1/1991 |
| EP | 0 505 686 | 9/1992 |
| EP | 0 513 818 | 11/1992 |
| EP | 0 792 657 | 9/1997 |
| EP | 0 801 955 | 10/1997 |
| EP | 1 059 954 | 12/2000 |
| EP | 1 066 080 | 1/2001 |
| EP | 1 156 847 | 11/2001 |
| EP | 1867305 | 12/2007 |
| EP | 2067454 | 6/2009 |
| EP | 2133043 | 12/2009 |
| GB | 2018600 | 10/1979 |
| JP | 7-47133 | 2/1995 |
| WO | WO 92/00775 | 1/1992 |
| WO | WO 92/03963 | 3/1992 |
| WO | WO 92/13589 | 8/1992 |
| WO | WO 92/17236 | 10/1992 |
| WO | WO 92/22345 | 12/1992 |
| WO | WO 93/00126 | 1/1993 |
| WO | WO 93/11826 | 6/1993 |
| WO | WO 93/17750 | 9/1993 |
| WO | WO 93/20882 | 10/1993 |
| WO | WO 94/03213 | 2/1994 |
| WO | WO 94/04216 | 3/1994 |
| WO | WO 94/11038 | 5/1994 |
| WO | WO 94/11047 | 5/1994 |
| WO | WO 94/15549 | 7/1994 |
| WO | WO 96/33764 | 10/1996 |
| WO | WO 98/10820 | 3/1998 |
| WO | WO 98/10821 | 3/1998 |
| WO | WO 99/08740 | 2/1999 |
| WO | WO 99/38557 | 8/1999 |
| WO | WO 99/44667 | 9/1999 |
| WO | WO 99/48552 | 9/1999 |
| WO | WO 99/49808 | 10/1999 |
| WO | WO 99/59664 | 11/1999 |
| WO | WO 00/69498 | 11/2000 |
| WO | WO 00/69499 | 11/2000 |
| WO | WO 00/69500 | 11/2000 |
| WO | WO 01/47591 | 7/2001 |
| WO | WO 02/074378 | 9/2002 |
| WO | WO 2005/053574 | 6/2005 |
| WO | WO 2011/035318 | 3/2011 |

OTHER PUBLICATIONS

Knecht, Gregory L., M.D. et al., "Double-Channel Fistulotome for Endoscopic Drainage of Pancreatic Pseudocyst", *Gastrointestinal Endoscopy*, vol. 37, No. 3, May/Jun. 1991, pp. 356-357.

Siegel, Jerome H., M.D. et al., "Two New Methods for Selective Bile Duct Cannulation and Sphincterotomy", *Gastrointestinal Endoscopy*, vol. 33, No. 6, Dec. 1987, pp. 438-440.

\* cited by examiner

STENT DELIVERY SYSTEMS AND METHODS FOR MAKING AND USING STENT DELIVERY SYSTEMS

CROSS-REFERENCE TO RELATED APPLICATION

This application claims priority under 35 U.S.C. § 119 to U.S. Provisional Application Ser. No. 61/501,387, filed Jun. 27, 2011, the entirety of which is incorporated herein by reference.

TECHNICAL FIELD

The present disclosure pertains to medical devices and methods for manufacturing medical devices. More particularly, the present disclosure pertains to stent delivery systems that include an attachment mechanism for securing a stent.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example stent delivery system may include a guide catheter. A push catheter may be slidably disposed over the guide catheter. A stent may be slidably disposed over the guide catheter and disposed adjacent to a distal end of the push catheter. A cantilever may be coupled to the push catheter.

Another example stent delivery system may include a guide catheter. A push catheter may be slidably disposed over the guide catheter. A stent may be slidably disposed over the guide catheter and disposed adjacent to a distal end of the push catheter. The stent may have an opening formed therein. A beam may be attached to the push catheter. The beam may be configured to shift between a first engaged configuration where the beam is engaged with the opening in the stent and a second unengaged configuration.

An example method of delivering a stent within a body lumen of a patient may include providing a stent delivery system. The stent delivery system may include a guide catheter. A push catheter may be slidably disposed over the guide catheter. A stent may be slidably disposed over the guide catheter and disposed adjacent to a distal end of the push catheter. The stent having an opening formed therein. A beam may be attached to the push catheter. The beam is configured to shift between a first engaged configuration where the beam is engaged with the opening in the stent and a second unengaged configuration. The method may include advancing the stent delivery system through a body lumen to a position adjacent to an area of interest. The method may include proximally retracting the guide catheter relative to the push catheter to shift the beam from the first configuration to the second configuration.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A wide variety of biliary, endoscopic, and/or endosurgical procedures have been developed for making medical treatments, diagnoses, and images of areas along the biliary tract and/or the pancreatic tract. For the purposes of this disclosure, the "biliary tract" and/or the "pancreatic tract" are understood to include various components of the digestive system and include, for example, the various ducts of the biliary tree between the liver and the duodenum as well as the various ducts between the pancreas and the duodenum. Numerous endoscopic and/or endosurgical devices have been developed for making medical treatments, diagnoses, and images of areas along the biliary and pancreatic tracts. Some of these device and/or procedures include biliary catheters, biliary guidewires, biliary stent delivery systems, drainage of the bile duct, splinting of the bile duct during healing, providing bile duct patency in a stricture or past a stone, and the like. In general, these devices are guided to the biliary and/or pancreatic tract by an endoscope (and/or a duodenoscope) that is disposed in the duodenum. Once positioned, various interventions can be performed depending on the needs of the patient and the type of device utilized. Other locations and/or uses are also contemplated for the systems disclosed herein including, for example, urinary tract interventions and/or urological interventions, gynecological interventions, etc.

When delivering a stent such as a drainage stent to the appropriate position within the anatomy, it may be desirable to hold or secure the position of the stent relative to a push catheter, which may be part of the stent delivery system. This allows the clinician to position and deploy the stent accurately at the intended location. One way that the stent may be secured to the push catheter may be with the use of a suture. Conventionally when a suture is utilized to secure a stent to a push catheter, the suture is formed into a loop that is wrapped around the guide catheter (which may extend through the lumen of the push catheter). The suture then extends through one of the barbed openings or flaps formed in the stent and it may be pulled snugly and attached or tied to the end of the push catheter, for example at a hole or opening formed at the distal end of the push catheter. As long as the position of the guide catheter is held stationary relative to the push catheter, this arrangement holds the position of the stent and effectively secures the stent to the push catheter. To release the stent, the guide catheter can be proximally retracted to a point where it exits and is disposed proximally of the loop formed in the suture. When no longer wrapped around the guide catheter, the loop or looped end of the suture is free to simply exit the opening at the barbed flap of the stent such that the stent is released from the push catheter.

Disclosed herein are a number of delivery systems for delivering a stent (e.g., a drainage stent) to an appropriate position within the anatomy. The delivery systems may use an attachment mechanism to secure the position of the stent relative to a push member or catheter. The attachment mechanism may allow a clinician to selectively "lock" and "unlock" a stent to the push catheter so that the stent can be accurately deployed to a target site. The use of the attachment mechanism disclosed herein may be desirable for a number of reasons. For example, the attachment mechanism disclosed herein allows the deployment of a stent while the guidewire is left in place. This allows the clinician to maintain guidewire access within the anatomy throughout the intervention. In addition, the attachment mechanism disclosed herein may allow a clinician to deploy and/or reposition the stent multiple times with just one system. Additionally, the attachment mechanism may be formed from materials that allow for improved visualization at the treatment including radiopaque materials. Moreover, the attachment mechanism disclosed herein may help control or otherwise fix the distance between the push catheter and the stent, which may increase the accuracy in deployment. Furthermore, the attachment mechanism disclosed herein may eliminate the need for sutures, which may be expensive and labor intensive to use. In addition, manufacturing the attachment mechanism disclosed herein (and/or the delivery systems incorporating the attachment mechanism) may be possible in an automated or semi-automated manner so that manufacturing costs can be reduced. These are just examples. Some additional details regarding these and other features are provided below.

Figure 1:
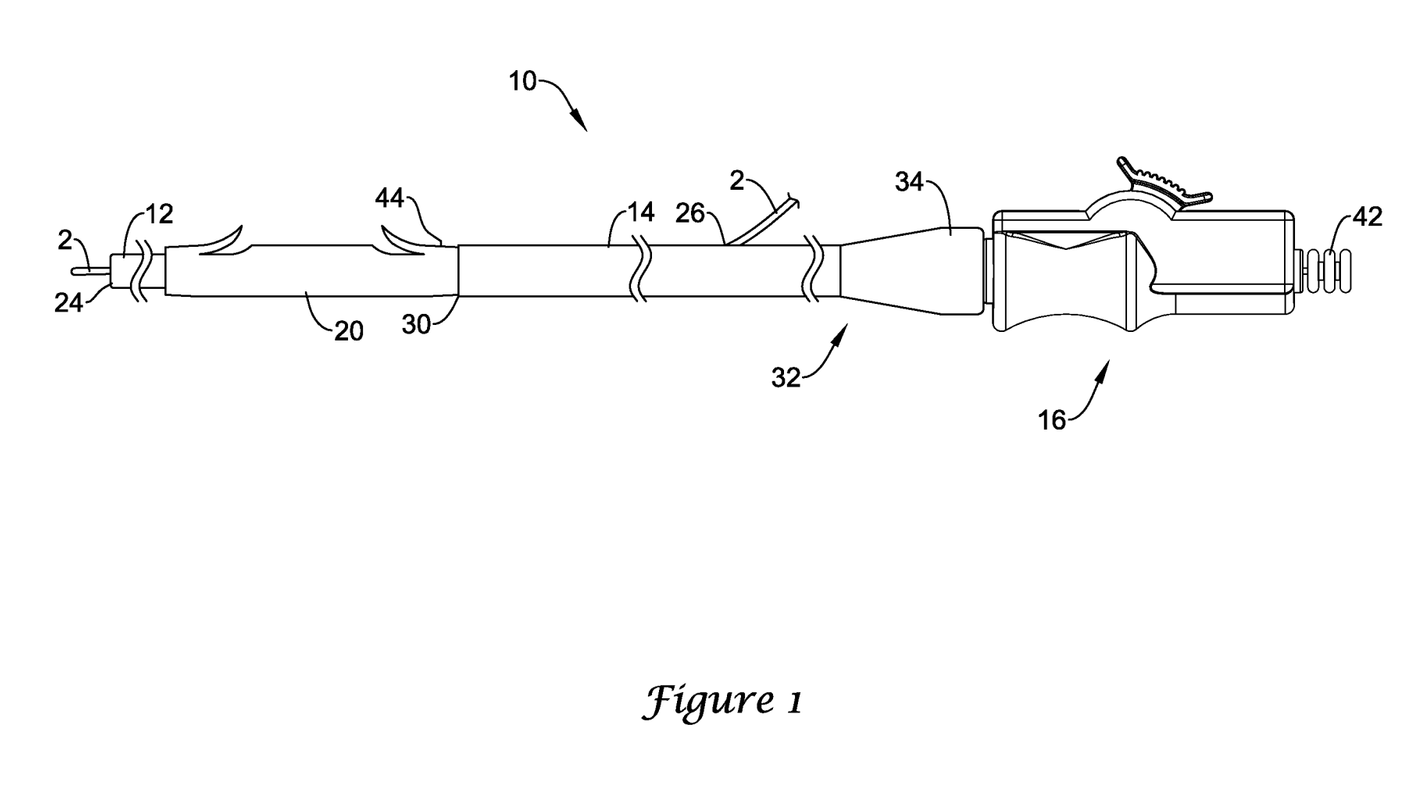
FIG. 1 is a side view of an example stent delivery system.
Figure 2:
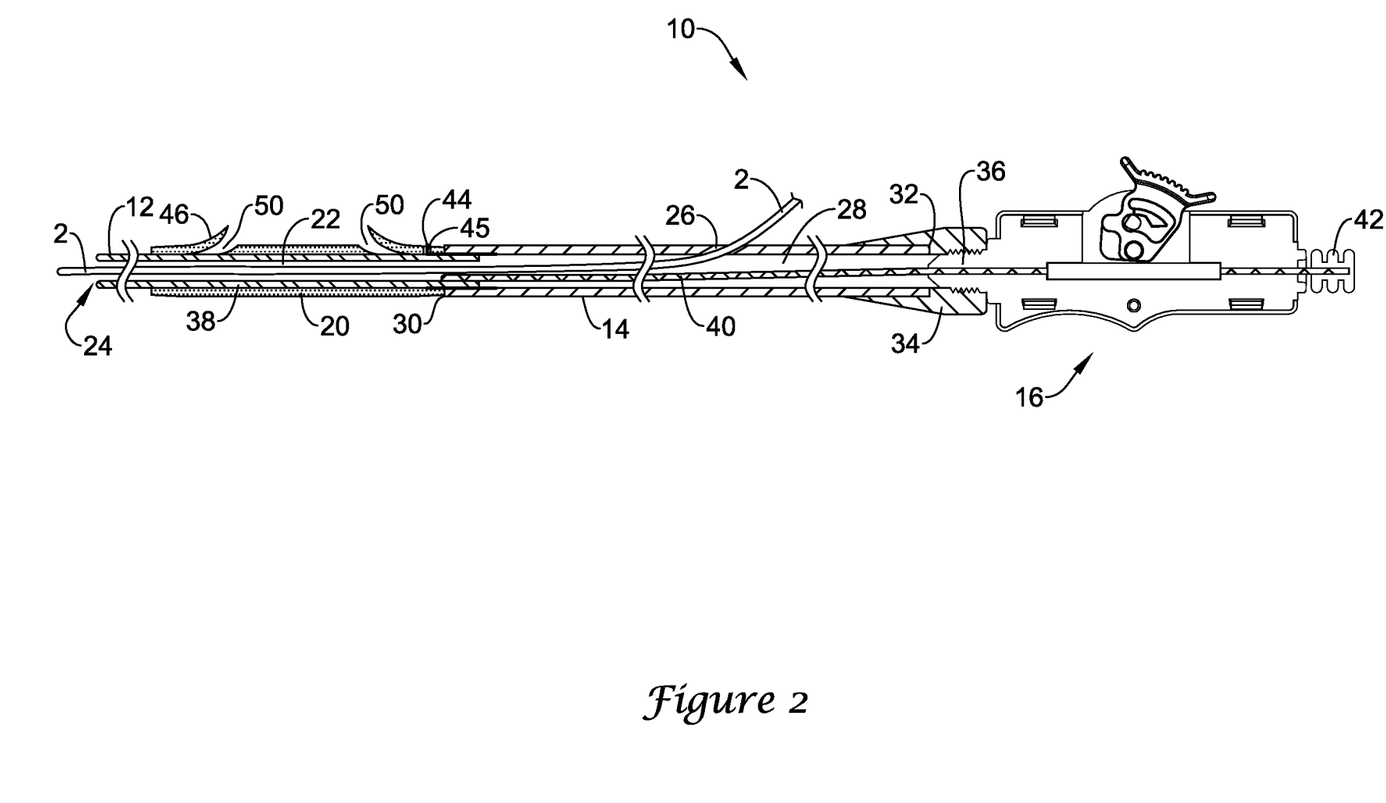
FIG. 2 is a partial cross-sectional side view of the example stent delivery system of FIG. 1.

Referring now to FIGS. 1 and 2, there is shown an example medical device, illustrated as a delivery system 10 for delivering, for example, a stent 20 such as a drainage stent to a suitable target location such as, for example, a target along the biliary and/or pancreatic tree. The system 10 may also be used at any other suitable location. The stent 20 may be used to bypass or drain an obstructed lumen, for example along the biliary and/or pancreatic tree, and can be configured for long-term positioning within the body. It should be understood that the terms "drainage stent", "drainage catheter" and "stent" can be used interchangeably with reference to the devices and systems disclosed herein.

The delivery system 10 may be designed for use with a conventional guidewire 2 and may include a guide catheter 12, a delivery or push catheter 14, and a handle assembly 16. The guidewire 2 may extend into a lumen 22 of the guide catheter 12, through a distal guidewire port 24, and out a proximal guidewire port 26 formed in a sidewall of the push catheter 14, providing the delivery system 10 with single-operator-exchange (SOE) capabilities. Other embodiments are also contemplated, however, where the delivery system 10 is an over-the-wire (OTW) system.

The guide catheter 12 may be slidably disposed within the lumen 28 of the push catheter 14 and may extend distally from the distal end of the push catheter 14. The stent 20 may be positioned on a distal portion of the guide catheter 12, which may be located distal of the push catheter 14, and the stent 20 may abut or otherwise be disposed adjacent to the distal end 30 of the push catheter 14. When the stent 20 has been properly placed, the stent 20 may be disconnected from the push catheter 14 such that the stent 20 remains in the anatomy or body lumen when the push catheter 14 is withdrawn.

The proximal end 32 of the push catheter 14 may be attached to the handle assembly 16. For example, the proximal end 32 may include a female luer lock connector 34 threadably coupled to a threaded male connector 36 of the handle assembly 16. It may be understood, however, that the push catheter 14 may be attached to the handle assembly 16 and extend distally therefrom by other means, such as adhesive bonding, welding, friction fit, interlocking fit, or other suitable means.

The guide catheter 12 may include a distal tubular portion 38 and a proximal elongate wire 40, such as a pull wire, coupled to the distal tubular portion 38. In some instances, the elongate wire 40 may be a wire, filament, thread, portion of a catheter wall, fabric, web, or similar elongate structure. The elongate wire 40 may be coupled to the distal tubular portion 38 at a rotatable connection that may allow rotatable movement between the tubular portion 38 and the elongate wire 40 of the guide catheter 12. The elongate wire 40 may extend through the lumen 28 of the push catheter 14 to the handle assembly 16. In some embodiments, the elongate wire 40 may extend through the handle assembly 16 to a location proximal of the handle assembly 16. The proximal end of elongate wire 40 may terminate at a knob 42 which may be grasped by an operator to manipulate the guide catheter 12.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

The stent 20 may include one or more anchors 46 that are generally disposed near an opening 50 in the stent 20. Anchors 46, for example, may project radially outward from the stent 20 and help to secure or "anchor" the position of the stent 20 within the anatomy when deployed. In at least some embodiments, the anchors 46 are defined by a skived cut in the stent 20 and take the form of a barb or barb-like flap. Other configurations are contemplated.

As indicated above, the system 10 may also include an attachment mechanism 44. In general, the attachment mechanism may be configured to secure the position of the stent 20 relative to the push catheter 14. To do so, the attachment mechanism 44 may have a portion that extends through a hole or opening 45 formed in the stent 20. Note that in some cases, the hole or opening 45 may be positioned proximally from the barb openings 50 in the stent 20. In other embodiments, however, the attachment mechanism 44 may engage one of the barb openings 50, thereby reducing or eliminating the need for dedicated openings 45. In some embodiments, the hole 45 extends through the wall of the stent 20 while in others the hole 45 may extend through only a portion of the wall of the stent 20 or otherwise take the form of a groove.

Figure 3:
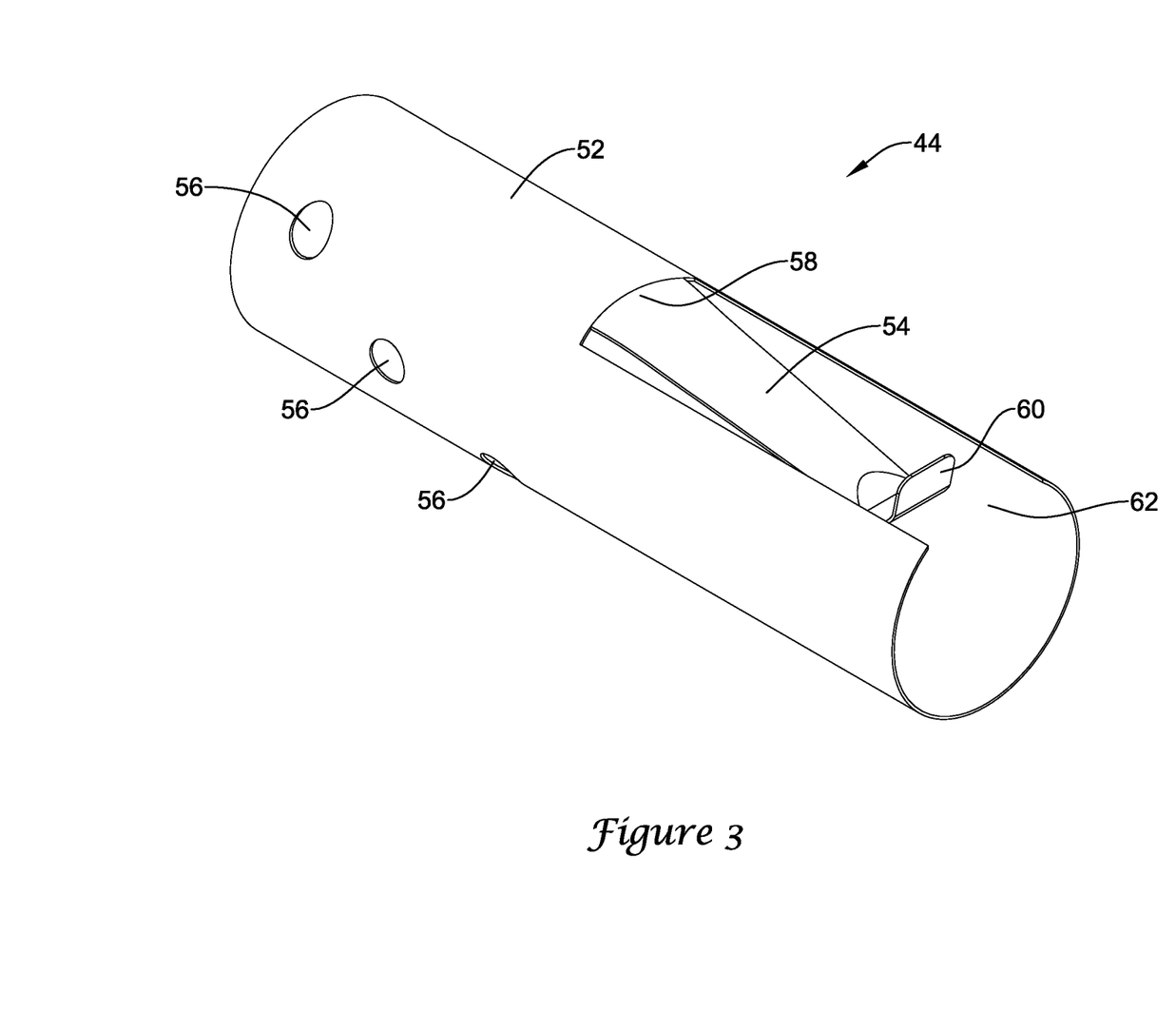
FIG. 3 is a perspective view of an example attachment mechanism.

The example attachment mechanism 44 may include a generally cylindrical base 52 and a beam or cantilever 54 extending from the base 52 as shown in FIG. 3. The length of the cantilever 54 extending from the base 52 may vary. For example, attachment mechanisms 44 are contemplated where the length of the cantilever 54 is relatively short as compared to the base 52 (e.g., the length is only a portion of the length of the base 52) and other attachment mechanisms are contemplated where the length of the cantilever 54 approximates or approaches the length of the base 52. In at least some embodiments, the base 52 may be disposed between the guide catheter 12 and the push catheter 14. For example, the base 52 may be attached to the push catheter 14. To facilitate bonding between the base 52 and the push catheter 14, the base 52 may include one or more retention holes 56. For example, the push catheter 14 may be molded into the retention holes 56 in the attachment mechanism 44 to create a bond between the push catheter 14 and the attachment mechanism 44. Alternatively, the attachment mechanism 44 may be attached to the push catheter 14 by an adhesive, by welding or soldering, by a thermal bond, or using any other suitable manner. In some cases, the attachment mechanism 44 may be modified to further enhance the bond to the push catheter 14 by applying an abrasive finish, a ribbed surface, a barbed surface, a threaded surface or surfaces, a snap-in mechanism such as a matching groove and bumps, or by creating an interference fit between the inner diameter of the push catheter 14 and the outer diameter of the cylindrical base 52 of the attachment mechanism 44. These are just examples.

Note that in some cases, the attachment mechanism 44 may be omitted completely. In at least some of these cases, a cantilever or beam (e.g., which may be similar to the cantilever 54) may extend from the stent 20 toward the guide catheter 12, or may extend from the guide catheter 12 toward the stent 20, without the use of an attachment mechanism 44. In some cases, the cantilever or beam may be a wire with an upward bend.

The attachment mechanism 44 may be formed in any suitable manner. For example, the attachment mechanism 44 may be formed from a metal tube or cannula that is cut by punch and die tooling, laser cutting, electron discharge machining, or other suitable techniques. Alternatively, the attachment mechanism may be thermoformed by injection molding. These are just examples as other forming techniques are contemplated.

The size, shape, and/or configuration of the attachment mechanism 44 may also improve the accuracy of stent 20 deployment. For example, because the cantilever 54 may have an essentially constant length and because the base 52 may be fixed to the push catheter 14, the precise position of the stent 20 relative to the push catheter 14 may be known. This controls the distance between the stent 20 and the push catheter 14 using the dimensionally controlled cantilever 54. Because of this, the clinician may be able to reliably determine where the stent 20 is located based on the position of the push catheter 14. Moreover, if the attachment mechanism 44 includes a radiopaque material, fluoroscopic visualization may also be relied upon to accurately determine the position of the stent 20.

The cantilever 54 may have a fixed proximal end 58, which is fixed to the cylindrical base 52, and may have a free distal end 60 that extends away from the fixed proximal end 58. In this example, the cylindrical base 52 may include a longitudinal notch 62 extending proximally from a distal edge of the cylindrical base 52, with the cantilever 54 extending distally from a proximal edge of the notch 62. The base 52 may form a support wall that allows the stent 20 to be better aligned and supported by the attachment mechanism 44. The cantilever 54 may extend substantially parallel to a longitudinal axis of the guide catheter 12.

The cantilever 54 may be configured to shift between a first or "locked configuration" and a second or "unlocked" configuration. When in the locked configuration, the cantilever 54 may be oriented so that the distal end 60 projects into or otherwise engages the opening 45 in the stent 20 such that the stent 20 is substantially "locked" or otherwise fixed to the push catheter 14. When in the unlocked configuration, the cantilever 54 shifts (e.g., radially inward) so that the distal end 60 disengages from the opening 45 in the stent 20 such that the stent 20 is no longer fixed to the push catheter 14.

Figure 4:
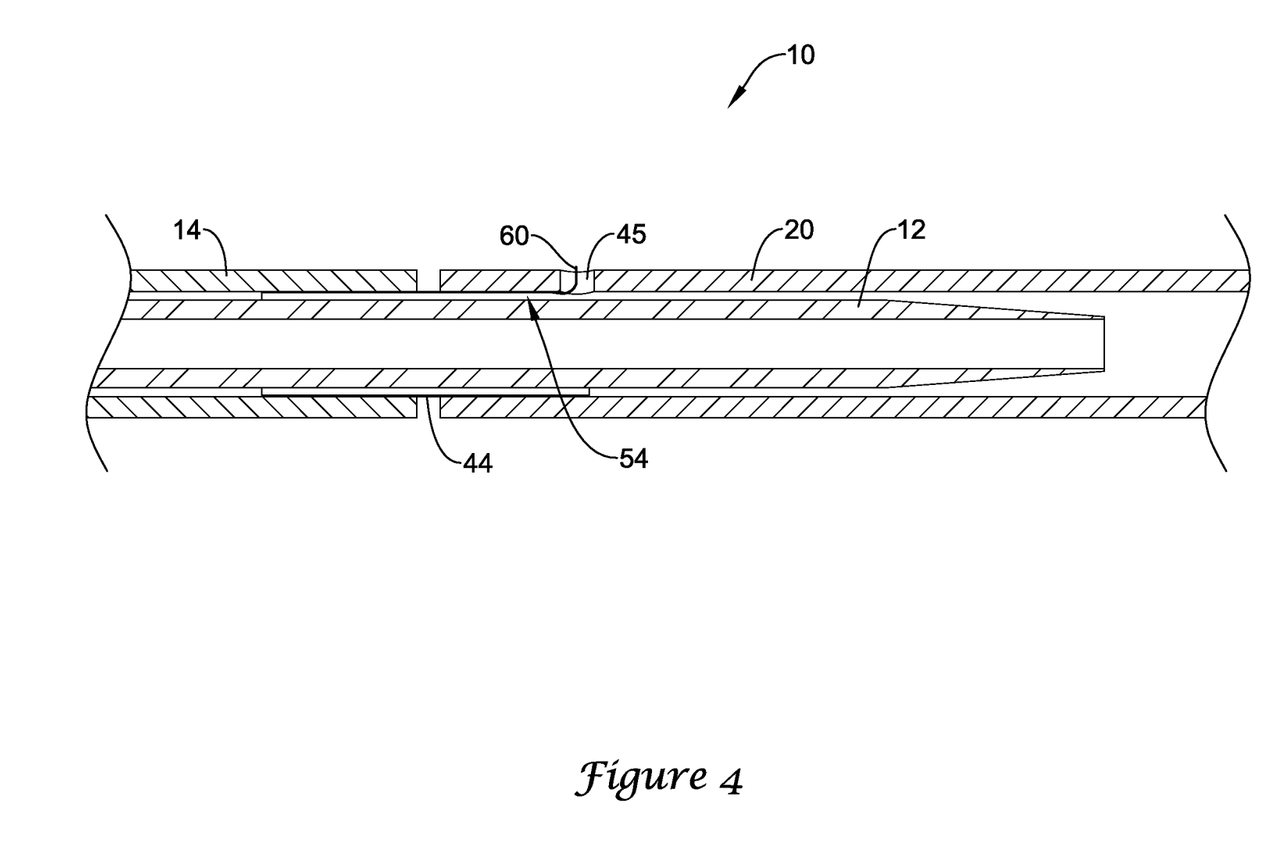
FIG. 4 is a cross-sectional side view of an example stent delivery system with the attachment mechanism in a locked configuration.
Figure 5:
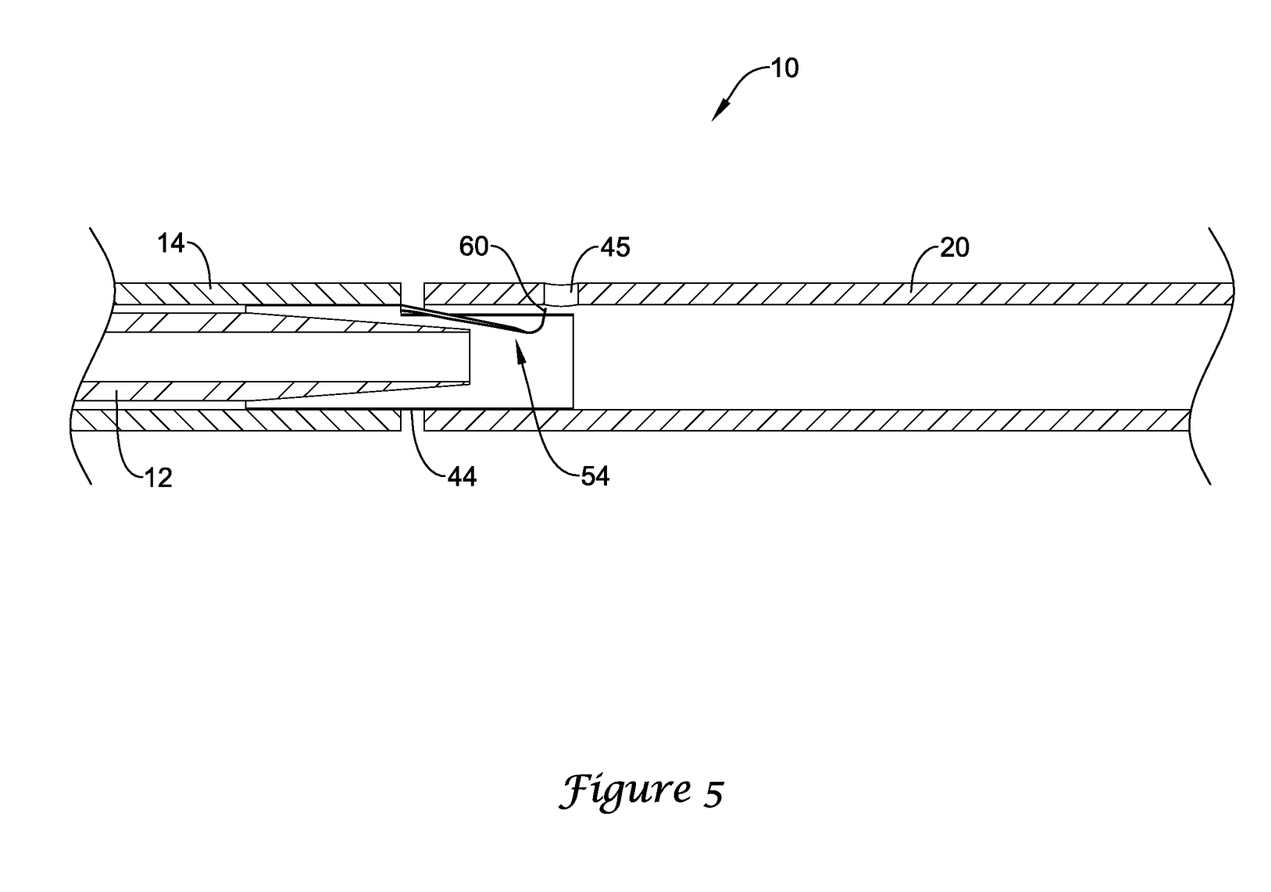
FIG. 5 is a cross-sectional side view of an example stent delivery system with the attachment mechanism in a locked configuration.
Figure 6:
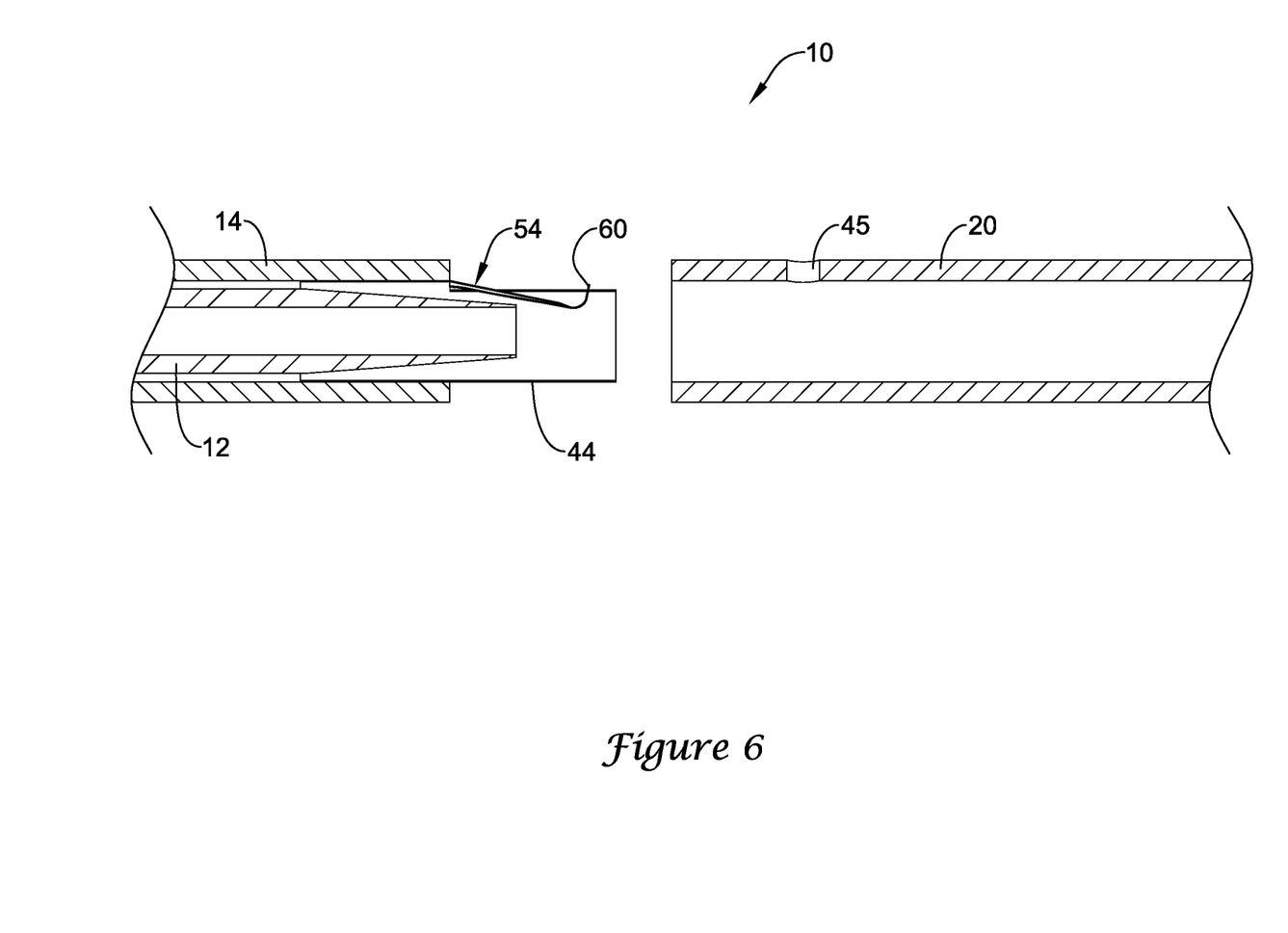
FIG. 6 is a cross-sectional side view of an example stent delivery system with the attachment mechanism in a locked configuration.

The cantilever 54 may form a hinge or pivot point adjacent to the proximal end 58 that allows the cantilever 54 to move, for example, radially outward and inward. For example, the cantilever 54 may be pre-bent or curved radially inward. In at least some embodiments, the cantilever 54 may be biased to be in this pre-bent configuration. This may correspond to the unlocked configuration. The cantilever 54 may be shifted between the locked and unlocked configuration by the guide catheter 12. For example, when the guide catheter 12 is passed through the attachment mechanism 44, the guide catheter 12 may engage and urge radially outward the cantilever 54 and, thus, shifts it to the locked configuration as shown in FIG. 4. In other words, the cantilever 54 may be biased to be in the unlocked configuration and advancing the guide catheter 12 through the attachment mechanism 44 overcomes the bias. When in the locked configuration, the distal end 60 of the cantilever 54 may extend through the opening 45 of the stent 20. When the guide catheter 12 is retracted proximally, the guide catheter 12 no longer engages the cantilever 54 and the cantilever 54 may deflect radially inward and disengage from the opening 45 in the stent 20 as shown in FIG. 5. When the cantilever 54 is in the unlocked configuration, the stent 20 is released from the push catheter 14 and the stent 20 can be deployed as shown in FIG. 6.

Because the configuration of the cantilever 54 may be altered by movement of the guide catheter 12, the clinician may have control of the stent 20 and may be able to hold/secure the stent 20 and then release/deploy the stent 20 "on demand". In addition, because shifting of the cantilever 54 is accomplished through movement of the guide catheter 12, the guidewire 2 can be left in place during deployment of the stent 20, which provides greater flexibility for the clinician because access to the appropriate location in the anatomy can be maintained throughout the intervention.

The attachment mechanism 44 may be made of any suitable materials including any of those disclosed herein. For example, the attachment mechanism 44 may be made from stainless steel, nitinol, tantalum, and tungsten. Alternatively, the attachment mechanism 44 may be made from a polymer including, for example, PEEK (polyetheretherketone), ABS (acrylonitrile-butadienestyrene), Nylon, Polyester, Ultem (PEI, or Polyether Imide), LCP (liquid crystal polymer), HDPE (high-density polyethylene) or LDPE (low-density polyethylene). These are just examples. In some cases, the attachment mechanism 44 may be made of or otherwise include a radiopaque material that can be viewed under fluoroscopy to aid in properly placing the stent 20.

Figure 7:
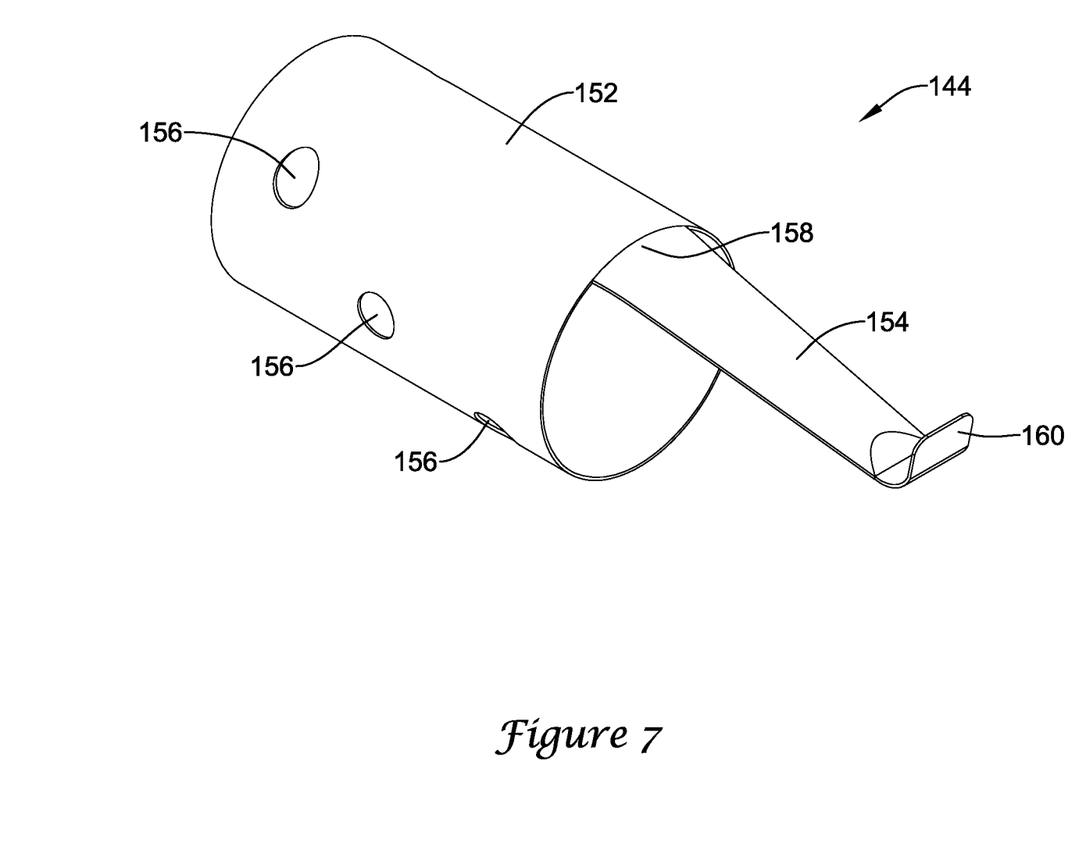
FIG. 7 is a perspective view of another example attachment mechanism.

FIG. 7 is a perspective view of another example attachment mechanism 144, which may be similar in form and function to the attachment mechanism 44, and may be utilized with the delivery system 10. The attachment mechanism 144 includes a cylindrical base 152 and retention holes 156. In this example, rather than being disposed within a notch in the base 152, the cantilever or beam extends distally from the base 152. For example, the proximal end 158 is attached or fixed to the base 152 and projects distally therefrom. This may increase the flexibility of the attachment mechanism 144 and, thus, the delivery system that it is incorporated into. The distal end 160 of the cantilever 154 may engage the opening 45 of the stent 20 in a manner similar to how the distal end 60 of the attachment mechanism 44 does.

In the examples disclosed herein, the attachment mechanisms 44/144 only include one cantilever or beam 54/154. This, however, is not intended to be limiting. Embodiments are contemplated where the attachment mechanism 44/144 includes more than one cantilever 54/154. For example, the attachment mechanism 44/144 may include two, three, four, five, six, or more cantilevers 54/154 arranged in any suitable manner. In these embodiments, the stent 20 may also include corresponding openings (e.g., similar to opening 45) for each of the cantilevers. In some cases, more than one cantilever may lock into the same hole or opening (e.g., the opening 45) in the stent 20. In some cases, the inclusion of two opposing cantilevers may allow the delivery system 10 to be used as a grasping device to remove and/or reposition stent 20. In addition, the distal end 60/160 of the cantilevers 54/154 may include a projection that projects radially inward, which may further improve the ability of the cantilevers 54/154 to remove and/or reposition the stent 20.

Note that cantilever 54 is not required to have any particular width or thickness. However, the geometry and material of cantilever 54 may be chosen to control the release of the stent 20. End 60 is not limited to the tab as shown. For instance, the end 60 may be a peg or bump, or may include more than one tab or peg.

In some cases, the cantilever may not be a solid element or beam, but may include one or more hollow portions that extend through the cantilever. For instance, the cantilever may include one or more holes that extend vertically through the cantilever. In some cases, the cantilever may be formed as a wire, extending longitudinally from the attachment mechanism, forming a loop that extends laterally and also extends vertically so that the vertical portion can engage the hole or groove in the stent, and then extends longitudinally to attach at its opposite end at the attachment mechanism. For these cases, the attachment points may be relatively close together so that the longitudinally extending portions are generally parallel, or may be relatively far apart so that the longitudinally extending portions include a lateral component. In other cases, the cantilever may be formed as a single wire that is only affixed to the attachment mechanism at one end, where the other end terminates at or near an upward-extending hook. These are just examples.

In some cases, the aspect ratio of the beam or cantilever 54 may be relatively close to 1:1, or may even include a larger width than length.

In some cases, the mating hole in the stent 20 may not extend fully through the stent 20, or may be formed as a groove rather than a hole.

As alluded to herein, the delivery system 10 and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

In at least some embodiments, portions or all of the tubular member(s) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of tubular member in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the tubular member to achieve the same result.

In some embodiments, a degree of Magnetic Resonance Imaging (MRI) compatibility is imparted into the tubular member. For example, the tubular member, or portions thereof, may be made of a material that does not substantially distort the image and create substantial artifacts (i.e., gaps in the image). Certain ferromagnetic materials, for example, may not be suitable because they may create artifacts in an MRI image. The tubular member, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, a coating, for example a lubricious, a hydrophilic, a protective, or other type of coating may be applied over portions or all of the delivery system or components thereof. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The arrangement of the various structures of the delivery system 10 may vary. In some embodiments, the system 10 may include any of the structures or utilize any of the arrangements of structures that are disclosed in U.S. Pat. Nos. 5,152,749; 5,334,185; 5,921,952; 6,248,100; 6,264,624; and 6,562,024, the entire disclosures of which are herein incorporated by reference. In addition, U.S. Patent Application Ser. No. 61/415,660, filed Nov. 19, 2010, is also herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
a guide catheter;
a push catheter slidably disposed over the guide catheter;
a stent slidably disposed over the guide catheter and disposed adjacent to a distal end of the push catheter, the stent having an opening formed therein;
a cylindrical member disposed between the guide catheter and push catheter, the cylindrical member having a longitudinal notch formed therein; and
a cantilever disposed within the longitudinal notch, wherein the cantilever includes a proximal end fixed to the cylindrical member and a free distal end extending from the fixed proximal end, wherein the free distal end is configured to project into the stent opening.

2. The stent delivery system of claim 1, wherein the cantilever is configured to shift between a first secured configuration where the cantilever is engaged with the stent to secure the stent to the push catheter and a second unsecured configuration.

3. The stent delivery system of claim 2, wherein the cantilever is biased to be in the second configuration.

4. The stent delivery system of claim 2, wherein the cantilever is in the first configuration when the guide catheter extends through the push catheter.

5. The stent delivery system of claim 4, wherein the cantilever shifts from the first configuration to the second configuration when the guide catheter is withdrawn proximally relative to the push catheter.

6. The stent delivery system of claim 1, wherein the stent is a drainage stent.

7. The stent delivery system of claim 1, wherein the stent has at least one flap or barb formed therein.

8. The stent delivery system of claim 1, wherein the cantilever includes a radiopaque material.

9. The stent delivery system of claim 1, wherein the cylindrical member is attached to the push catheter.

10. A stent delivery system, comprising:
a guide catheter;
a push catheter slidably disposed over the guide catheter;
a stent slidably disposed over the guide catheter and disposed adjacent to a distal end of the push catheter, the stent having an opening formed therein;
a cylindrical member disposed between the guide catheter and push catheter, the cylindrical member having a longitudinal notch formed therein; and
a beam is disposed within the longitudinal notch, wherein the beam includes a proximal end fixed to cylindrical member and a free distal end extending from the fixed proximal end, wherein the beam is configured to shift between a first engaged configuration where the free distal end projects into the opening in the stent and a second unengaged configuration.

11. The stent delivery system of claim 10, wherein the beam is biased to be in the second configuration.

12. The stent delivery system of claim 10, wherein the beam is in the first configuration when the guide catheter extends through the push catheter.

13. The stent delivery system of claim 12, wherein the beam shifts from the first configuration to the second configuration when the guide catheter is withdrawn proximally relative to the push catheter.

14. The stent delivery system of claim 10, wherein the cylindrical member is attached to the push catheter.

15. A method of delivering a stent within a body lumen of a patient, comprising:
    advancing a stent delivery system through a body lumen to a position adjacent to an area of interest, the stent delivery system comprising:
        a guide catheter,
        a push catheter slidably disposed over the guide catheter,
        a stent slidably disposed over the guide catheter and disposed adjacent to a distal end of the push catheter, the stent having an opening formed therein,
        a cylindrical member disposed between the guide catheter and push catheter, the cylindrical member having a longitudinal notch formed therein, and
        a beam disposed within the longitudinal notch, wherein the beam includes a proximal end fixed to the cylindrical member and a free distal end extending from the proximal end, wherein the beam is configured to shift between a first engaged configuration where the free distal end projects into the opening in the stent and a second unengaged configuration; and
    proximally retracting the guide catheter relative to the push catheter to shift the beam from the first configuration to the second configuration.

16. The method of claim 15, wherein advancing the stent delivery system through a body lumen to a position adjacent to an area of interest includes advancing the stent delivery system while the beam is in the first configuration.

17. The method of claim 15, wherein the beam secures the stent to the push catheter when the beam is in the first configuration and wherein proximally retracting the guide catheter releases the stent from the push catheter.

18. The method of claim 15, further comprising advancing the guide catheter distally to shift the beam from the second configuration to the first configuration.

19. The method of claim 15, wherein the cylindrical member is attached to the push catheter.

* * * * *